US012752061B2

(12) United States Patent
Shluzas et al.

(10) Patent No.: US 12,752,061 B2
(45) Date of Patent: Oct. 6, 2026

(54) SYSTEM AND METHOD FOR MULTIPLE SITE DISPENSING OR INJECTION

(71) Applicant: CREDENCE MEDSYSTEMS, INC., Menlo Park, CA (US)

(72) Inventors: Alan E. Shluzas, San Carlos, CA (US); Allyson Jade Weiss, San Jose, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 0 days.

(21) Appl. No.: 19/291,915

(22) Filed: Aug. 6, 2025

(65) Prior Publication Data

US 2026/0041850 A1 Feb. 12, 2026

Related U.S. Application Data

(60) Provisional application No. 63/681,733, filed on Aug. 9, 2024.

(51) Int. Cl.
*A61M 5/315* (2006.01)
*A61M 5/50* (2006.01)

(52) U.S. Cl.
CPC ...... *A61M 5/31578* (2013.01); *A61M 5/5066* (2013.01)

(58) Field of Classification Search
CPC ............ A61M 5/31578; A61M 5/5066; A61M 2005/3152
See application file for complete search history.

(56) References Cited

U.S. PATENT DOCUMENTS

| | | | | | |
|---|---|---|---|---|---|
| 4,465,478 | A | 8/1984 | Sabelman et al. | | |
| 5,688,252 | A * | 11/1997 | Matsuda | A61M 5/2448 | 604/218 |
| 7,678,084 | B2 | 3/2010 | Judson et al. | | |
| 11,707,577 | B2 * | 7/2023 | Shetty | A61M 5/31558 | 604/290 |
| 2005/0165363 | A1 * | 7/2005 | Judson | A61M 5/31551 | 604/209 |
| 2006/0217670 | A1 * | 9/2006 | Cecchi | A61M 5/3134 | 604/209 |
| 2007/0060894 | A1 | 3/2007 | Dai et al. | | |

(Continued)

OTHER PUBLICATIONS

PCT International Search Report and Written Opinion for International Appln. No. PCT/US2025/040838, Applicant Credence Medsystems, Inc., dated Nov. 14, 2025.

*Primary Examiner* — Andrew H Nguyen
(74) *Attorney, Agent, or Firm* — Vista IP Law Group, LLP

(57) ABSTRACT

A system for injection includes a disposable portion and a reusable portion. The disposable portion includes a syringe body having proximal and distal ends, a syringe interior, and a disposable portion flange at the proximal end thereof, an injectable fluid disposed in the syringe interior, a stopper member disposed in the syringe interior, and a plunger member coupled to the stopper member, wherein the plunger member defines a rack gear including a plurality of rack gear teeth. The reusable portion is configured to be removably coupled to the disposable portion. The reusable portion includes a gear assembly including a pinion gear configured to sequentially advance the plunger member distally by a predetermined distance, and a finger flange coupled to the disposable portion flange.

16 Claims, 20 Drawing Sheets

(56) References Cited

U.S. PATENT DOCUMENTS

| | | | | |
|---|---|---|---|---|
| 2014/0088553 | A1* | 3/2014 | Hetherington | A61M 5/31511 604/211 |
| 2019/0307963 | A1 | 10/2019 | Locati et al. | |
| 2020/0306453 | A1* | 10/2020 | Langley | A61M 5/31575 |
| 2021/0112819 | A1* | 4/2021 | Hetherington | A61M 5/3158 |
| 2021/0178080 | A1* | 6/2021 | Shetty | A61M 5/31551 |
| 2021/0213205 | A1* | 7/2021 | Karlsson | A61M 5/24 |
| 2024/0139420 | A1 | 5/2024 | Pliskow et al. | |
| 2024/0285867 | A1* | 8/2024 | Arnett | A61M 5/31585 |

* cited by examiner

PRIOR ART

SYSTEM AND METHOD FOR MULTIPLE SITE DISPENSING OR INJECTION

The present application claims priority to U.S. Provisional Patent Application Ser. No. 63/681,733, filed on Aug. 9, 2024 and entitled "SYSTEM AND METHOD FOR MULTIPLE SITE DISPENSING OR INJECTION." This application includes subject matter similar to the subject matter described in the following co-owned U.S. patent applications: (1) Ser. No. 14/321,706, filed Jul. 1, 2014, and entitled "SAFETY SYRINGE", (2) Ser. No. 14/543,787, filed Nov. 17, 2014, and entitled "SYSTEM AND METHOD FOR DRUG DELIVERY WITH A SAFETY SYRINGE"; (3) Ser. No. 14/696,342, filed Apr. 24, 2015, and entitled "SYSTEM AND METHOD FOR SAFETY SYRINGE"; (4) Ser. No. 15/801,239, filed Nov. 1, 2017, and entitled "SYSTEM AND METHOD FOR SAFETY SYRINGE"; (5) Ser. No. 15/801,259, filed Nov. 1, 2017, and entitled "SYSTEM AND METHOD FOR SAFETY SYRINGE"; (6) Ser. No. 15/801,281, filed Nov. 1, 2017, and entitled "CARTRIDGE SAFETY INJECTION SYSTEM AND METHODS"; (7) Ser. No. 16/011,453, filed Jun. 18, 2018, and entitled "SYSTEM AND METHOD FOR SAFETY SYRINGE"; (8) Ser. No. 15/801,304, filed Nov. 1, 2017, and entitled "SYSTEM AND METHOD FOR SAFETY SYRINGE"; (9) Ser. No. 15/985,354, filed May 21, 2018, and entitled "SYSTEM AND METHOD FOR COLLECTING INJECTION INFORMATION"; "(10) Ser. No. 16/683,157, filed Nov. 13, 2019, and entitled "SYSTEM AND METHOD FOR MULTIPLE SITE INJECTION"; and (11) Ser. No. 18/222,579, filed on Jul. 17, 2023 and entitled "SYSTEM AND METHOD FOR MULTIPLE SITE DISPENSNG OR INJECTION". The contents of the above-mentioned applications are fully incorporated herein by reference as though set forth in full.

FIELD OF THE DISCLOSURE

The present disclosure relates generally to dispensing and/or injection systems, devices, and processes for facilitating various levels of control over fluid delivery, and more particularly to systems and methods related to dispensing and/or injection systems for serial delivery of multiple doses of dispensable or injectable substances.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a proximal/retracted position relative to the syringe body (4). The tubular needle shield (22) is "locked" in the distal/extended configuration, such that the needle shield (22) can no longer be returned to the proximal/retracted position, to prevent accidental needle sticks after injection.

Another embodiment of a safety syringe (24) is shown in FIGS. 4A and 4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possibly malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for prefilled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus, certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3 to 4B) and relatively high inventory and utilization expenses.

As used in this application, the term fluid includes gels, jelly, creams, oils, ointments, emulsions, suspensions, dispersions, serums, semi-solids, semi-liquids, and/or liquids. The fluid may be a hyaluronic acid (HA) gel. The fluid may include one or more of the following: bovine collagen, collagen stimulator, elastin, bioabsorbable polymers, hydrogels, calcium hydroxyapatite (CaHA) microspheres, carboxymethylcellulose, Poly-L-Lactic acid (PLLA), Poly-lactic-co-glycolic acid (PLGA), polymethylmethacrylate (PMMA) microspheres, lidocaine, autologous fat. These fluids may be of low or high viscosity. These fluids may be provided to the user sterile and pre-filled in the syringe. Delivery of high viscosity fluids, especially through small needles, may result in pressure build up in delivery systems, which may push stopper members and plunger members proximally and increase variability in the volume of fluid delivered. This problem is exacerbated during delivery of small volumes of fluids. Some medications are serially delivered to multiple sites in or on a patient during a single treatment. Serial fluid delivery systems may include many components that increase the cost of such systems. This problem is exacerbated by the disposable nature of serial fluid delivery systems. In addition to systems for injecting medications, other systems (i.e., dispensing systems) serially dispense medications to multiple sites on a patient during a treatment course. The treatment course may be a single dose, or multiple doses spaced over time.

There is a need for dispensing and/or injection systems which address shortcomings of currently-available configurations. In particular, there is a need for dispensing and/or injection systems that serially dispense and/or inject fluids at multiple sites on one patient. It is also desirable that such dispensing and/or injection assemblies may utilize the existing and relatively well-controlled supply chain of conventionally delivered pre-filled cartridges and other off-the-shelf components, and the corresponding assembly machinery and personnel. It is further desirable that such dispensing and/or injection assemblies have a reusable portion configured for use with a disposable portion. Moreover, it is desirable that such dispensing and/or injection assemblies include an anti-return feature configured to prevent unintended proximal movement of the stopper member and the plunger member. In addition, it is desirable that such dispensing and/or injection assemblies be capable of entering an aspiration mode that allows proximal movement of the stopper member and the plunger member.

SUMMARY

Embodiments are directed to dispensing and/or injection systems. In particular, the embodiments are directed to dispensing and/or injection systems for serial delivery of multiple doses of dispensable or injectable substances.

In one embodiment, a system for injection includes a disposable portion and a reusable portion. The disposable portion includes a syringe body having proximal and distal ends, a syringe interior, and a disposable portion flange at the proximal end thereof, an injectable fluid disposed in the syringe interior, a stopper member disposed in the syringe interior, and a plunger member coupled to the stopper member, wherein the plunger member defines a rack gear including a plurality of rack gear teeth. The reusable portion is configured to be removably coupled to the disposable portion. The reusable portion includes a gear assembly including a pinion gear configured to sequentially advance the plunger member distally by a predetermined distance, and a finger flange coupled to the disposable portion flange.

In one or more embodiments, the disposable portion is a syringe. The plunger member may include a plunger member handle coupled to a proximal end of the plunger member. The plunger member may have a protrusion configured to be disposed in the stopper member to couple the stopper member to the plunger member. The plunger member may have a flat distal end without any protrusions configured to be disposed in the stopper member.

In one or more embodiments, the gear assembly includes a sprocket; and a reduction gear operatively coupling the sprocket to the pinion gear. The reduction gear may include a large diameter reduction gear and a small diameter reduction gear. The sprocket may be configured to act on the large diameter reduction gear, and the small diameter reduction gear may be configured to act on the pinion gear. The pinion gear may include a large diameter pinion gear and a small diameter pinion gear. The reduction gear may be configured to act on the large diameter pinion gear, and the small diameter pinion gear may be configured to act on the rack gear on the plunger member.

In one or more embodiments, the reusable member includes a thumbpad member, a thumbpad lockout tab, and a thumbpad lockout latch. The thumbpad member may define a pawl at a distal end thereof. The pawl may be operatively coupled to the sprocket of the gear assembly. The sprocket may include a large diameter sprocket gear and a small diameter sprocket gear. The pawl may be configured to act on the large diameter sprocket gear. The small diameter sprocket gear may be configured to act on the reduction gear. The reusable member may include a return spring configured to move the thumbpad member proximally after the thumbpad member is advanced distally. The reusable member may include an anti-return ratchet configured to prevent backwards rotation of the reduction gear to thereby prevent proximal movement of the plunger member.

In one or more embodiments, the reusable member includes a mode switch configured to change the system between a dosing mode and an aspiration mode. Actuating the mode switch to the aspiration mode may move the anti-return ratchet out of engagement with the reduction gear to allow free rotation of the reduction gear and the pinion gear and proximal movement of the plunger member, and may move the thumbpad lockout latch into engagement with the thumbpad lockout tab to prevent distal movement of the thumbpad. The pawl may be operatively coupled to the mode switch to prevent dosing (i.e., distal movement of the thumbpad member) when in aspiration mode. Actuating the mode switch to the dosing mode may move the anti-return ratchet into engagement with the reduction gear to prevent free rotation of the reduction gear and the pinion gear and free proximal movement of the plunger member, and may move the thumbpad lockout latch out of engagement with the thumbpad lockout tab to allow distal movement of the thumbpad.

In one or more embodiments, the disposable portion and the reusable portion are configured to allow a user to insert the disposable portion into the reusable portion. The system may also include a manual finger flange configured to be coupled to the disposable portion flange, and a manual thumbpad configured to be coupled to a proximal end of the plunger member. Coupling the manual finger flange and the manual thumbpad to the disposable portion flange and the proximal end of the plunger member may configure the disposable portion for manual use by a user. The plunger member may include a barbed peg at a proximal end thereof. The system may include an oblong shaped free-spinning thumbpad rotatably coupled to the barbed peg at the proximal end of the plunger member. The thumbpad may not be rotatably relative to the plunger member. In such embodiments, the plunger rod and the thumbpad may be configured to rotate relative to the stopper member, rendering the thumbpad rotatably coupled to the system.

The aforementioned and other embodiments of the invention are described in the Detailed Description which follows.

Figure 1A:
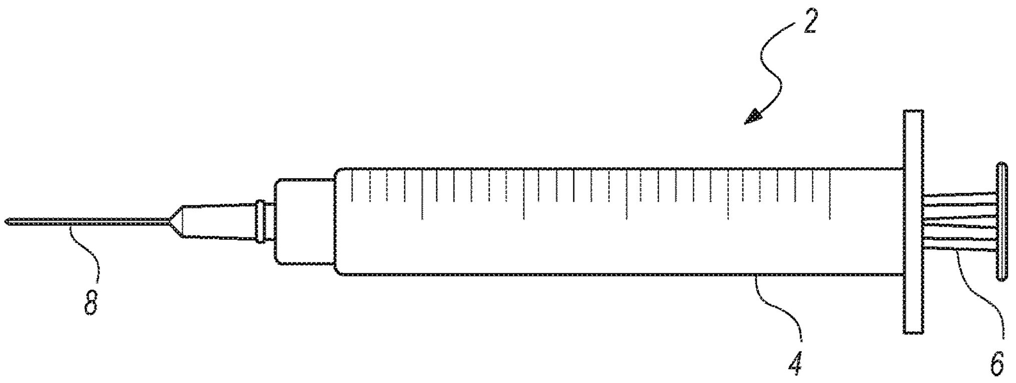
FIG. 1A PRIOR ART
FIGS. 1A to 5C illustrate various aspects of conventional injection syringe configurations.
Figure 1B:
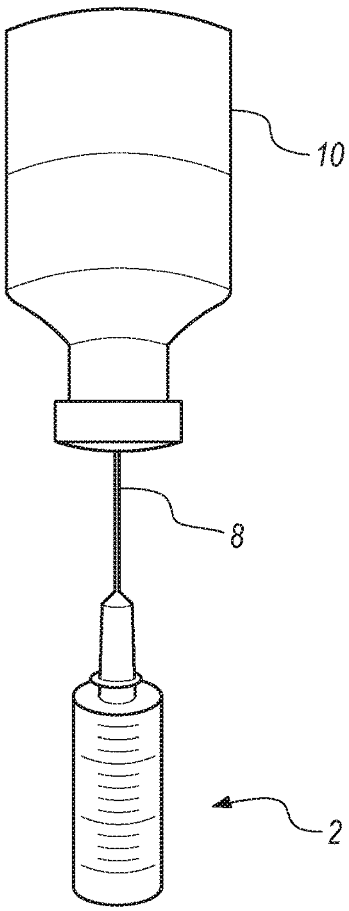
FIG. 1B PRIOR ART
Figure 2A:
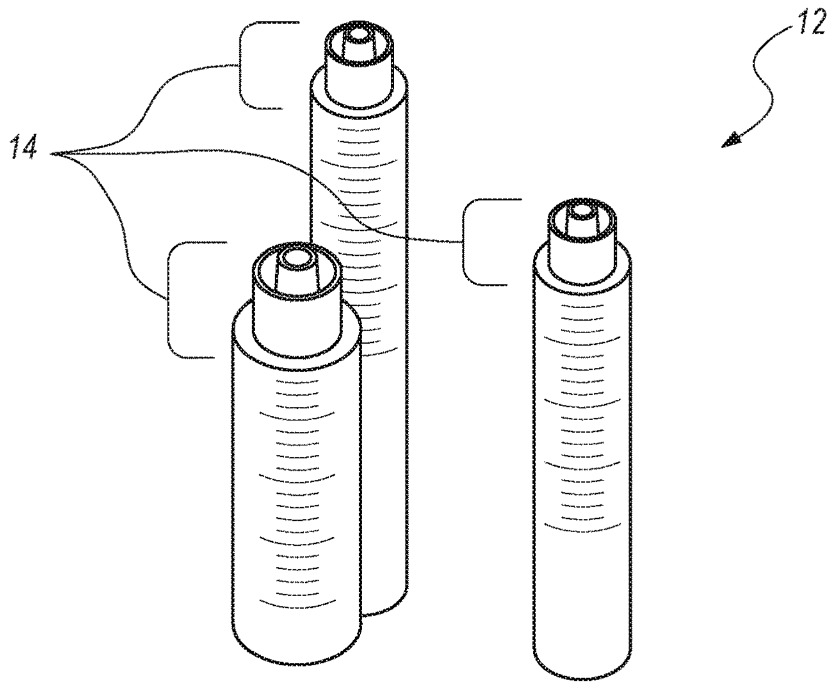
FIG. 2A PRIOR ART
Figure 2B:
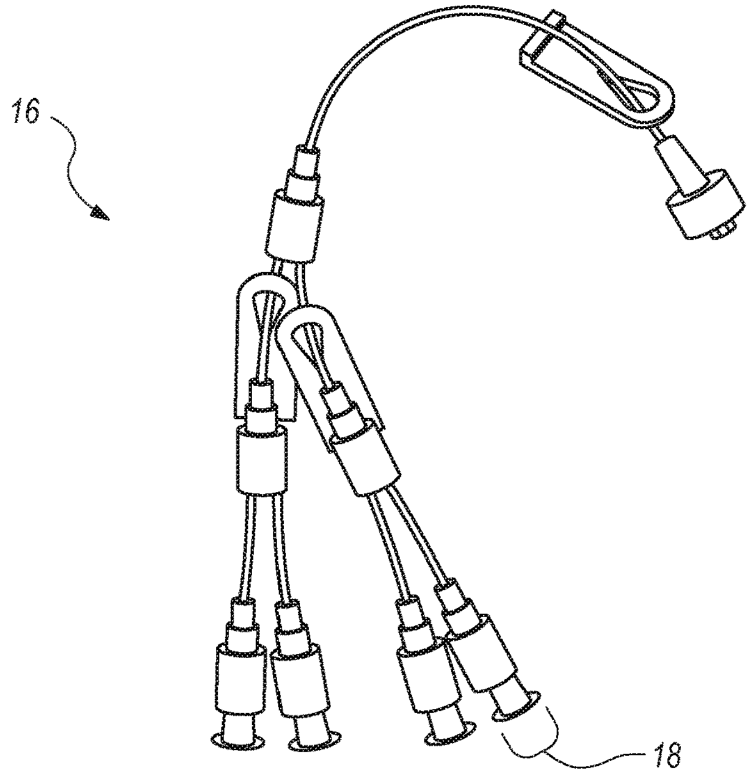
FIG. 2B PRIOR ART
Figure 3:
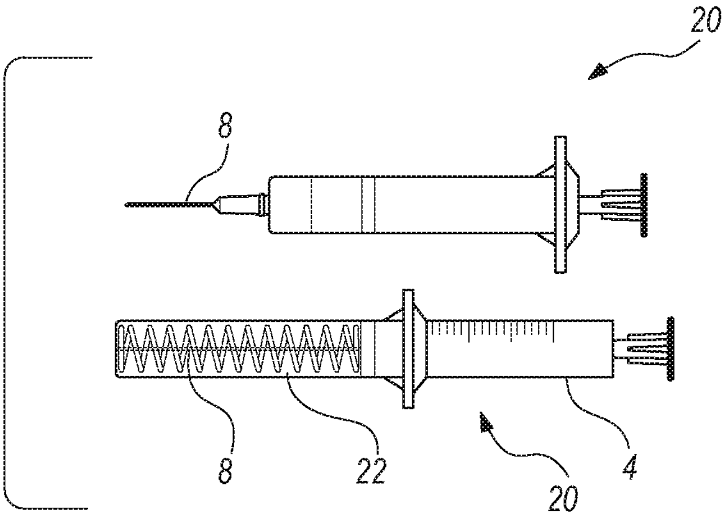
Figure 4A:
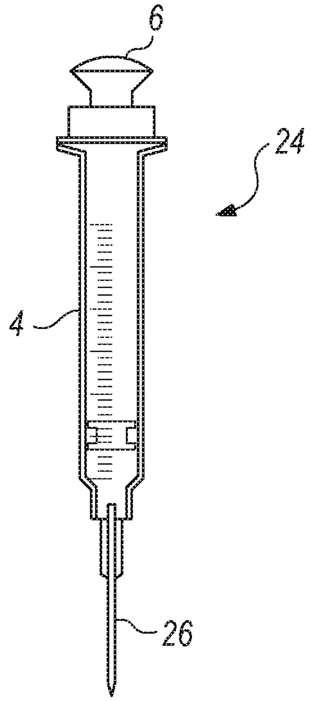
FIG. 4A PRIOR ART
Figure 4B:
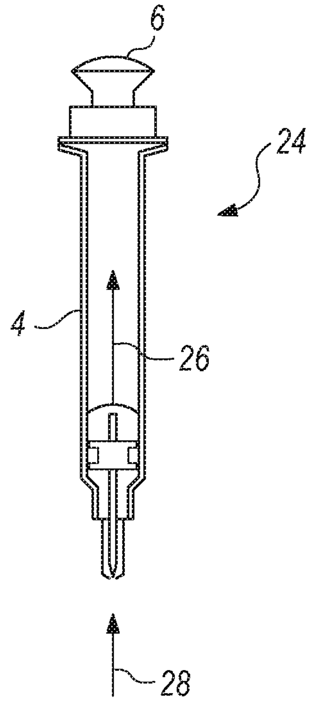
FIG. 4B PRIOR ART
Figure 5A:
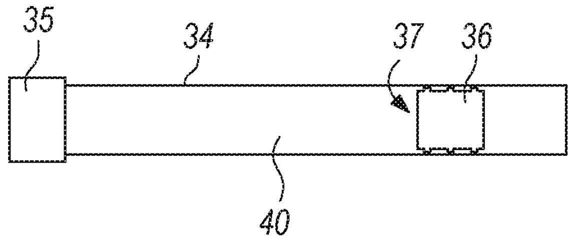
FIG. 5A PRIOR ART
Figure 5B:
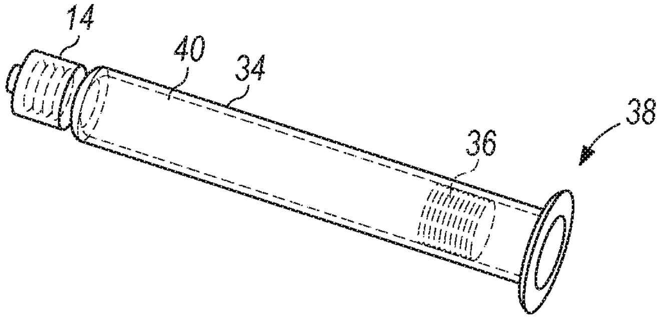
FIG. 5B PRIOR ART
Figure 5C:
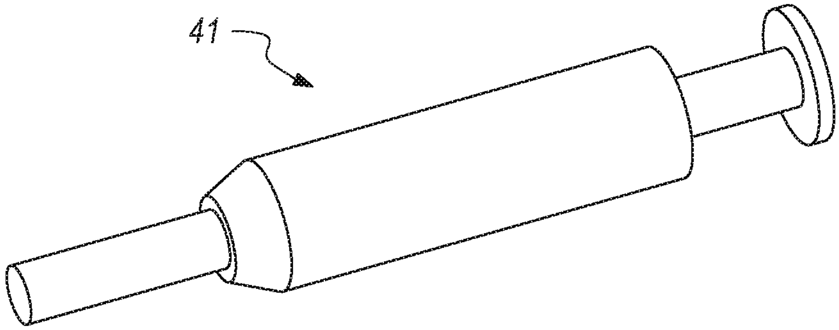
FIG. 5C PRIOR ART

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Multiple Site/Serial Dispensing and/or Injection Systems

Many dispensable or injectable medications can be administered to multiple dispensing, application, and/or injection sites on the same patient. Some medical procedures involve serial dispensing, application, and/or injection of fixed volumes (e.g., 10 μl) of medications at multiple dispensing, application, and/or injection sites on a patient. Currently, many medicines are drawn into a dispensing and/or injection system from a vial, which increases procedure time and exposure of a needle for unintended punctures. Further, some medications are delivered in a viscous solution, and therefore require a larger diameter (e.g., lower gauge: 25 g) needle to be used to draw the viscous medication into the dispensing and/or injection system and a smaller diameter (e.g., higher gauge: 30 g, 32 g, 34 g, sub-34 g) needle to be used for an injection. This exchange of needles results in increased procedure time and risk of unintended punctures.

Delivery of high viscosity fluids, especially through small needles, may result in pressure build up in delivery systems, which may push stopper members and plunger members proximally and increase variability in the volume of fluid delivered. This problem is exacerbated during delivery of small volumes (e.g., 10 μl) of fluids. Some medications are serially delivered to multiple sites in or on a patient during a single treatment. Serial fluid delivery systems may include many components that increase the cost of such systems. This problem is exacerbated by the disposable nature of serial fluid delivery systems.

The multiple site dispensing and/or injection system described herein addresses these issues of current systems. It is also desirable that such dispensing and/or injection assemblies may utilize the existing and relatively well-controlled supply chain of conventionally delivered pre-filled cartridges and other off-the-shelf components, and the corresponding assembly machinery and personnel. It is further desirable that such dispensing and/or injection assemblies have a reusable portion configured for use with a disposable portion. Moreover, it is desirable that such dispensing and/or injection assemblies include an anti-return feature configured to prevent unintended proximal movement of the stopper member and the plunger member. In addition, it is desirable that such dispensing and/or injection assemblies be capable of entering an aspiration mode that allows proximal movement of the stopper member and the plunger member.

Figure 6:
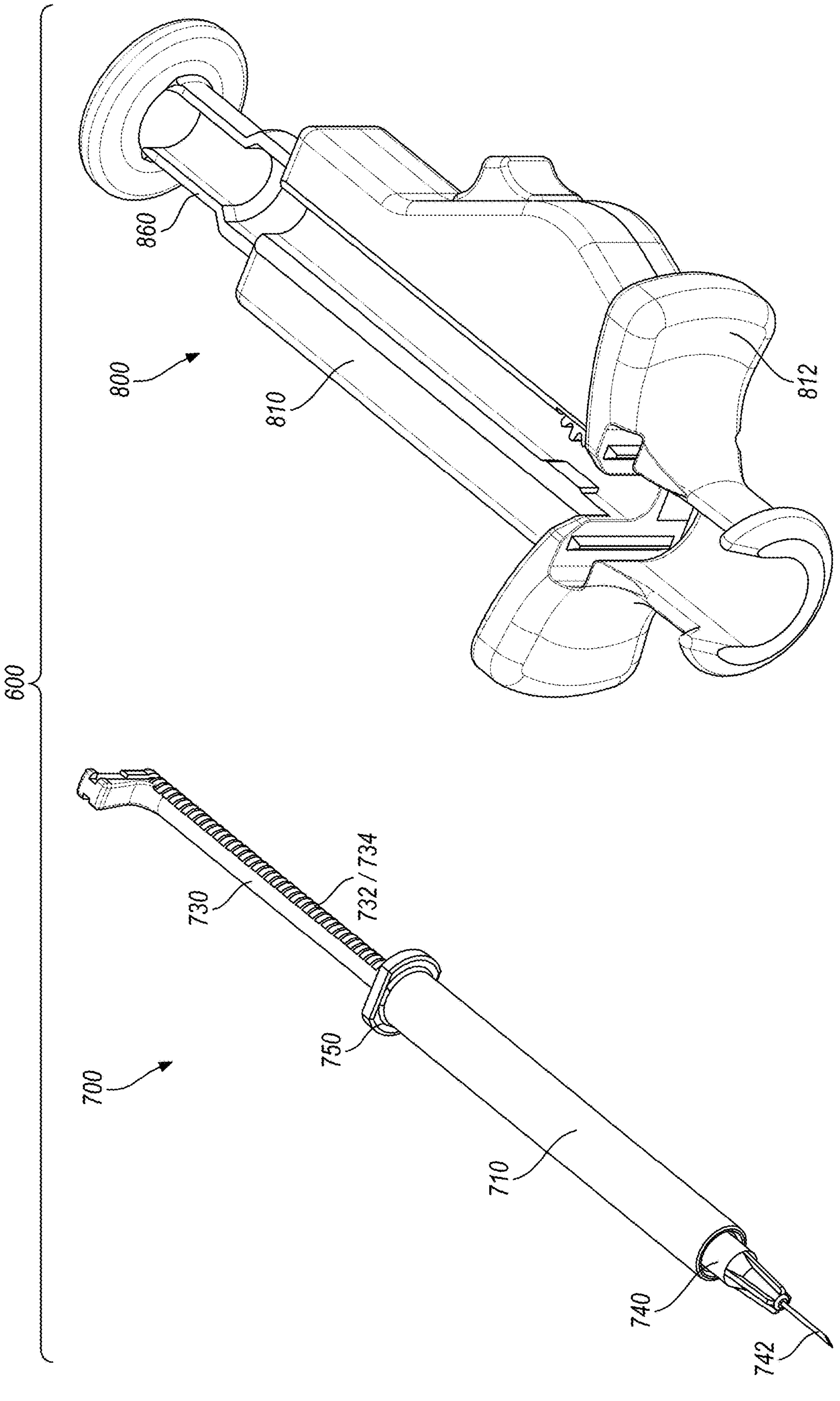
FIG. 6 is a front perspective view of a disposable portion and a reusable portion of a multiple site/serial injection system before assembly according to some embodiments.

FIGS. 6 to 15 depict a multiple site dispensing and/or injection system 600 according to some embodiments. FIG. 6 is a front perspective view of a disposable portion 700 and a reusable portion 800 of a multiple site/serial injection system 600 before assembly according to some embodiments. The disposable portion 700 includes a disposable portion body 710 having a stopper member 720 (see FIG. 9) disposed in an interior thereof and a disposable portion flange 750 at a proximal end thereof. The disposable portion 700 also includes a plunger member 730 coupled to the stopper member 720 and extending out an open proximal end of the disposable portion body 710. The plunger member 730 defines a rack gear 732 having a plurality of rack gear teeth 734. The disposable portion 700 optionally includes a needle hub assembly 740 having a needle 742 and coupled to the disposable portion body 710 at a distal end thereof. The disposable portion body 710 also includes a needle hub coupling member 714 (e.g., a female Luer connector; see FIG. 9) configured to removably couple the needle hub assembly 740, other dispensing mechanism (not shown), or applicator tip (not shown) thereto. The disposable portion body 710 of the disposable portion 700 can be prefilled with a dispensable or injectable medication.

Many of these system components (e.g., the syringe body 710 and the stopper member 720, and needle hub 740) may be off-the-shelf components to utilize the existing and relatively well-controlled supply chain, and the corresponding assembly machinery and personnel. The syringe body 710 may be glass, metal, or polymeric materials such as COC, COP, polypropylene, polyethylene, or other syringe material. The stopper member 720 may be rubber such as butyl, chlorobutyl, bromobutyl, or a polymeric material such as a thermoplastic elastomer. The stopper member 720 may be covered in a protective and/or lubricious coating such as PTFE or other polymer. The stopper member 720 being off-the-shelf refers to a commercially available stopper member, which has a generally smooth distally facing surface which contains no projections or recesses for coupling to a needle.

The reusable portion 800 includes a reusable portion body 810 that defines a finger flange 812 at a distal end thereof. The reusable portion 800 also includes a thumbpad member 860 disposed at a proximal end of the reusable portion body 810. The reusable portion 800 further includes a mode switch 870 operable to change the reusable portion between a dosing mode and an aspiration mode (see FIGS. 9 and 14).

Figure 7:
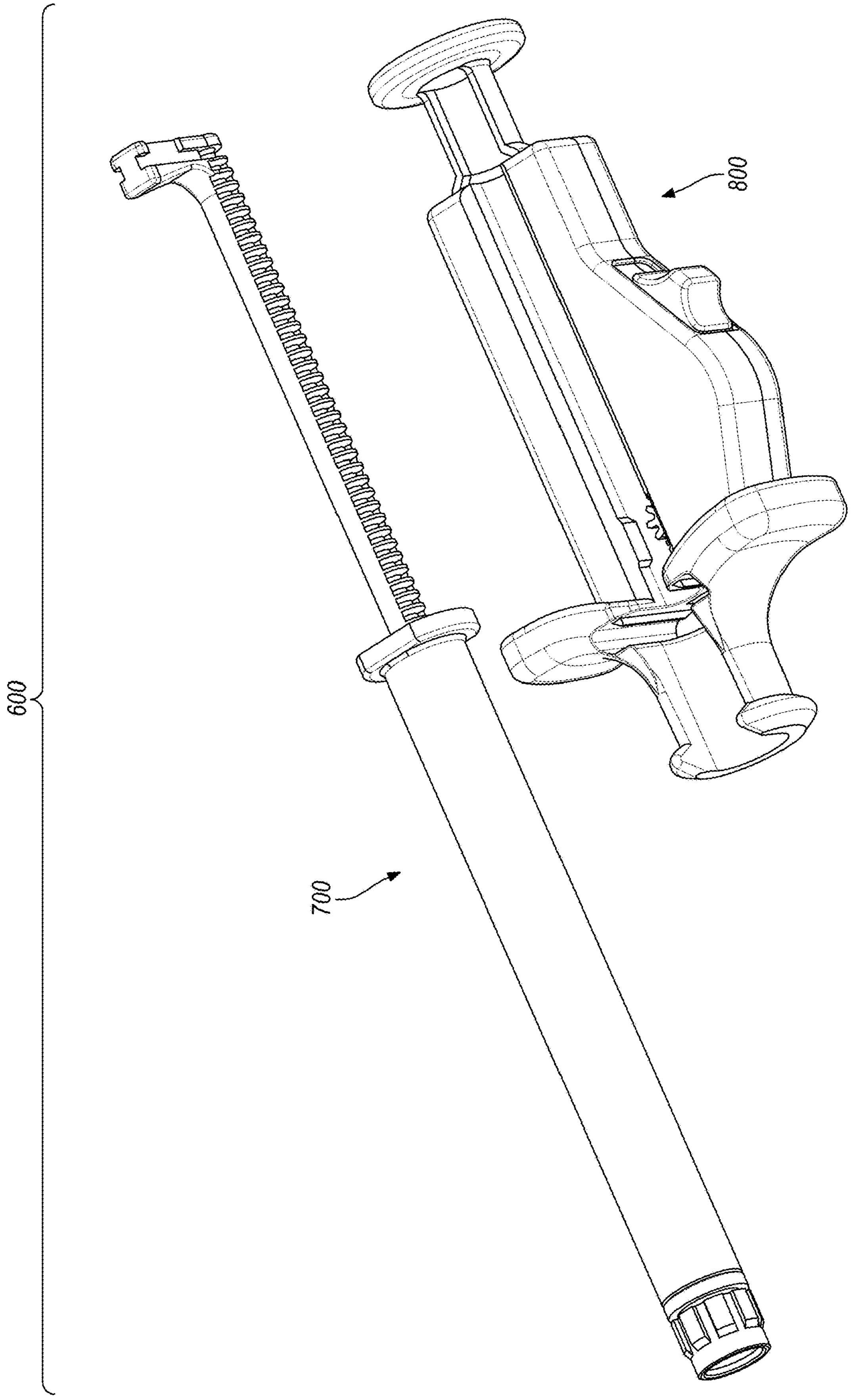
FIG. 7 is a front perspective view of the multiple site/serial injection system depicted in FIG. 6 during assembly according to some embodiments.

FIG. 7 is a front perspective view of the multiple site/serial injection system 600 depicted in FIG. 6 during assembly according to some embodiments. The disposable portion 700 is positioned adjacent the reusable portion 800 such that it can be inserted sideways into the reusable portion 800.

Figure 8:
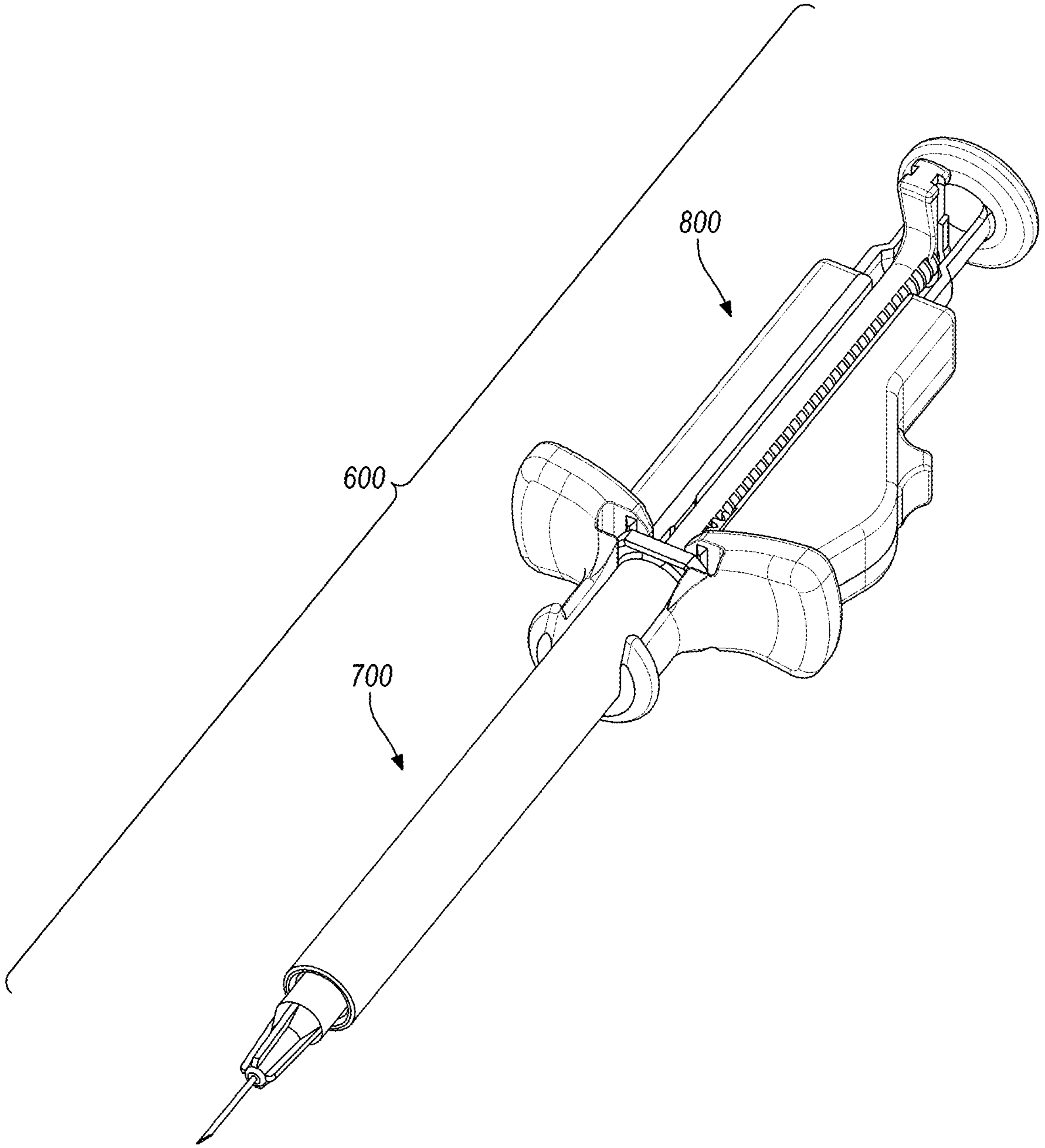
FIG. 8 is a front perspective view of the multiple site/serial injection system depicted in FIGS. 6 and 7 after assembly according to some embodiments.

FIG. 8 is a front perspective view of the multiple site/serial injection system 600 depicted in FIGS. 6 and 7 after assembly according to some embodiments. The disposable portion 700 has been inserted sideways into the reusable portion 800.

Figure 9:
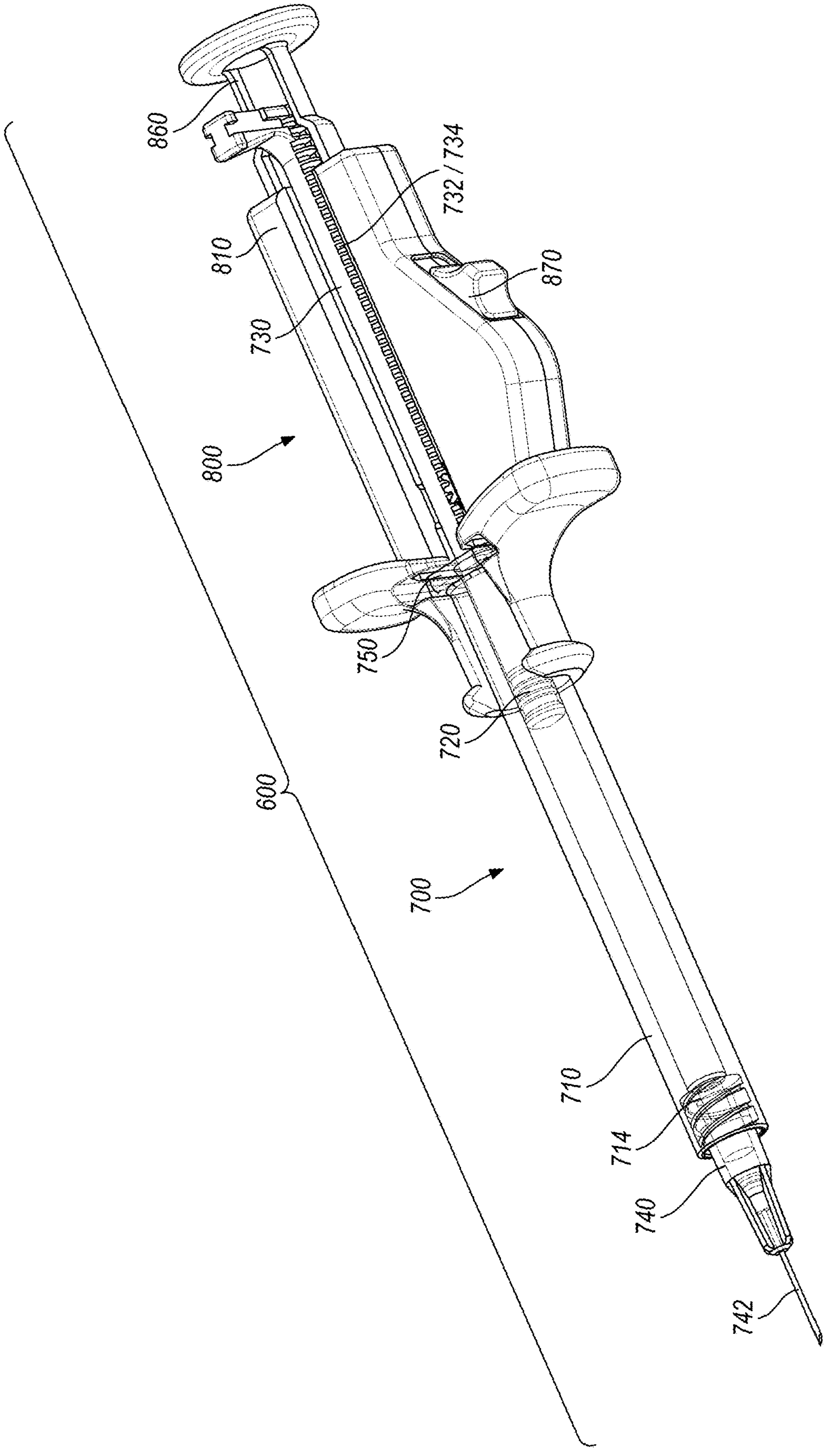
FIG. 9 is a front perspective view of a multiple site/serial injection system in a ready for dose configuration according to some embodiments.

FIG. 9 is a front perspective view of a multiple site/serial injection system in a ready for dose configuration according to some embodiments. In the ready for dose configuration, the plunger member 730 of the disposable portion 700 with its rack gear 732 and plurality of rack gear teeth 734 is disposed in the reusable portion 800. Further, the mode switch 870 of the reusable portion 800 is in a distal/dosing position. Moreover, the thumbpad member 860 is in a proximal/ready for dose position relative to the reusable portion body 810. This prepares the multiple site/serial injection system 600 for delivery of a dose of fluid/medication.

Figure 10:
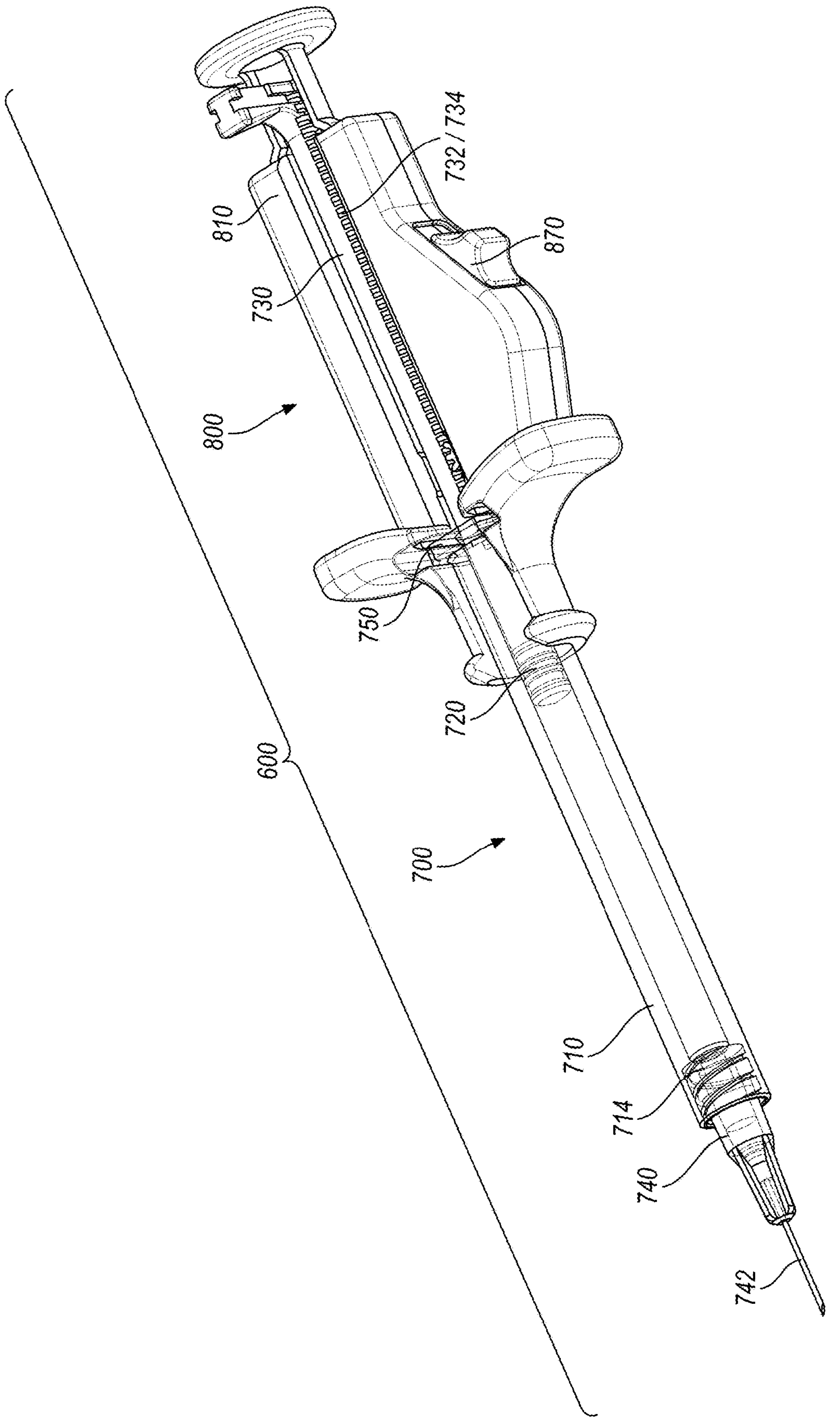
FIG. 10 is a front perspective view of a multiple site/serial injection system in an end of dose configuration according to some embodiments.

FIG. 10 is a front perspective view of a multiple site/serial injection system in an end of dose configuration according to some embodiments. In the end of dose configuration, a distally directed force has been applied to the thumbpad member 860 to move the thumbpad member 860 distally relative to the reusable portion body 810 to a distal/end of dose position. Moving the thumbpad member 860 distally moves the plunger member 730 and the stopper member 720 distally relative to the disposable portion body 710 a predetermined distance to eject/inject a predetermined dose (e.g., 10 μl) of fluid/medication from an interior of the disposable portion body 710. The distance and dose can be predetermined by tuning various components of the reusable portion 800 (see FIGS. 11 to 13).

Figure 11:
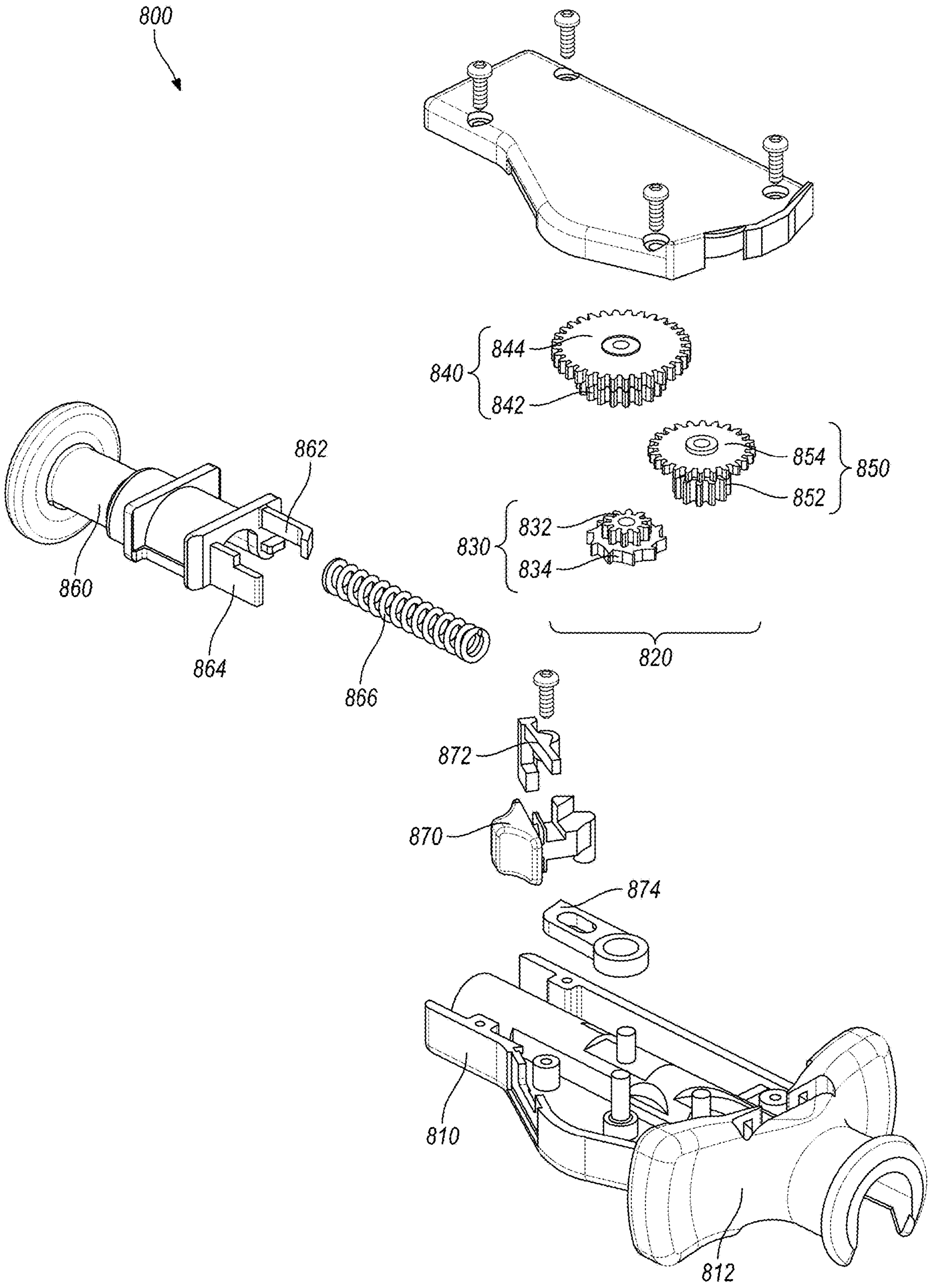
FIG. 11 is an exploded view of a reusable portion of a multiple site/serial injection system according to some embodiments.

FIG. 11 is an exploded view of a reusable portion 800 of a multiple site/serial injection system 600 according to some embodiments. The reusable portion 800 includes a reusable portion body 810 and a thumbpad member 860. The thumbpad member 860 defines a pawl 862 and a thumbpad lockout tab 864 at a distal end thereof. The reusable portion 800 also includes a spring 866 configured to move the thumbpad member 860 proximally after the thumbpad member 860 is advanced distally.

The reusable portion 800 also includes a gear assembly 820, which includes a sprocket 830, a reduction gear 840, and a pinion gear 850. The sprocket 830 includes a small diameter sprocket gear 832 and a large diameter sprocket gear 834, which are rotationally coupled. The reduction gear 840 includes a small diameter reduction gear 842 and a large diameter reduction gear 844, which are rotationally coupled. The pinion gear 850 includes a small diameter pinion gear 852 and a large diameter pinion gear 854, which are rotationally coupled.

The reusable portion 800 also includes a mode switch 870 configured to change the multiple site/serial injection system 600 between a dosing mode and an aspiration mode. The reusable portion 800 further includes an anti-return ratchet 872 configured to prevent proximal movements of the plunger member 730 and the stopper member 720 when the multiple site/serial injection system 600 is in the dosing mode. Moreover, the reusable portion 800 includes a thumbpad lockout latch 874 configured to interfere with the thumbpad lockout tab 864 when the multiple site/serial injection system 600 is in the aspiration mode to prevent distal movements of the thumbpad member 860.

Figure 12:
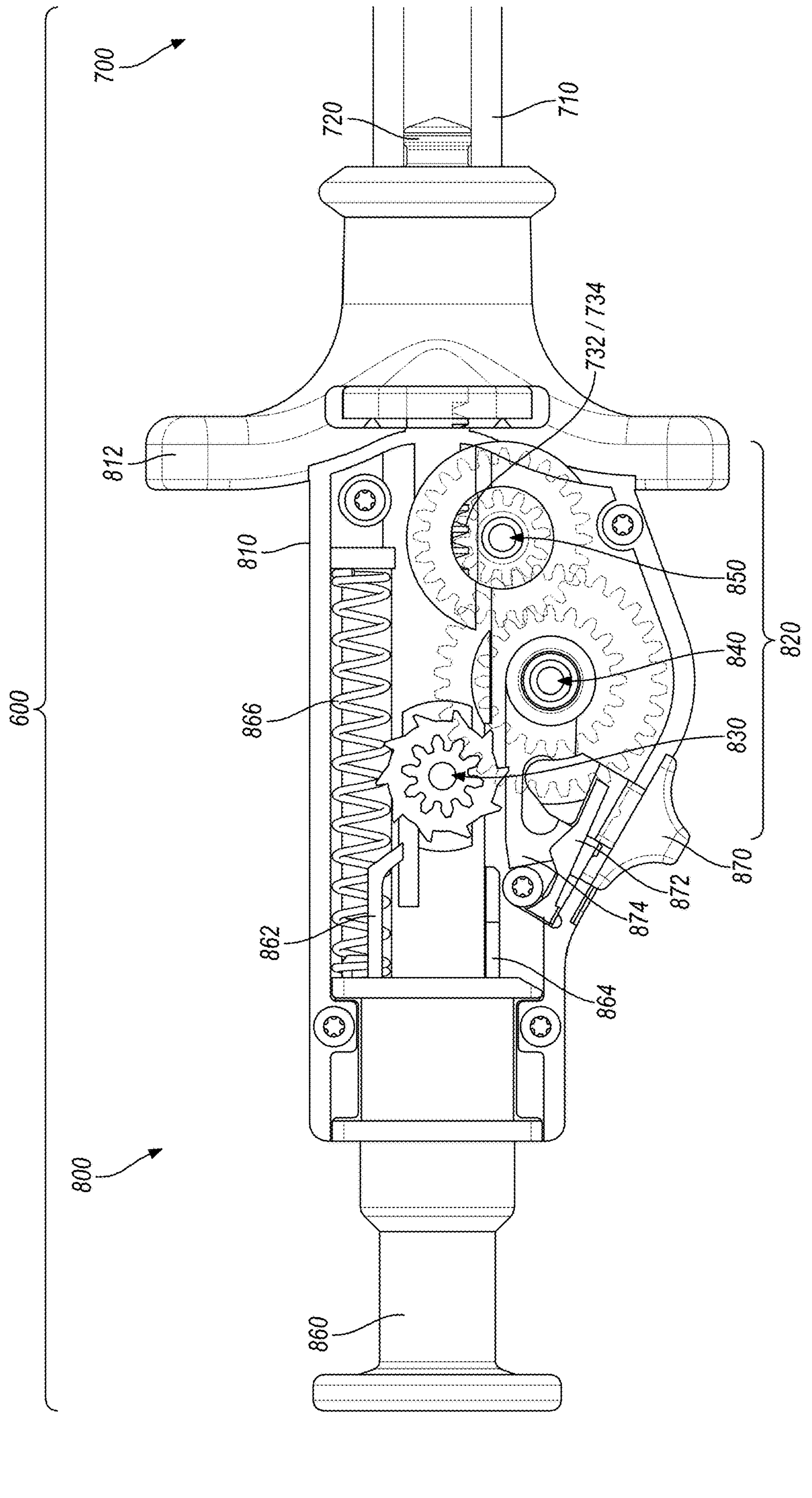
FIG. 12 is a detailed slide view of a multiple site/serial injection system in a ready for dose configuration with a portion of the system body omitted to show internal components according to some embodiments.

FIG. 12 is a detailed slide view of a multiple site/serial injection system 600 in a ready for dose configuration (see FIG. 9) with a portion of the reusable portion body 810 omitted to show internal components according to some embodiments. In the ready for dose configuration, the mode switch 870 of the reusable portion 800 is in a distal/dosing position. Further, the thumbpad member 860 is in a proximal/ready for dose position relative to the reusable portion body 810 and the spring 866 is in an expanded configuration. This prepares the multiple site/serial injection system 600 for delivery of a dose of fluid/medication.

Figure 13:
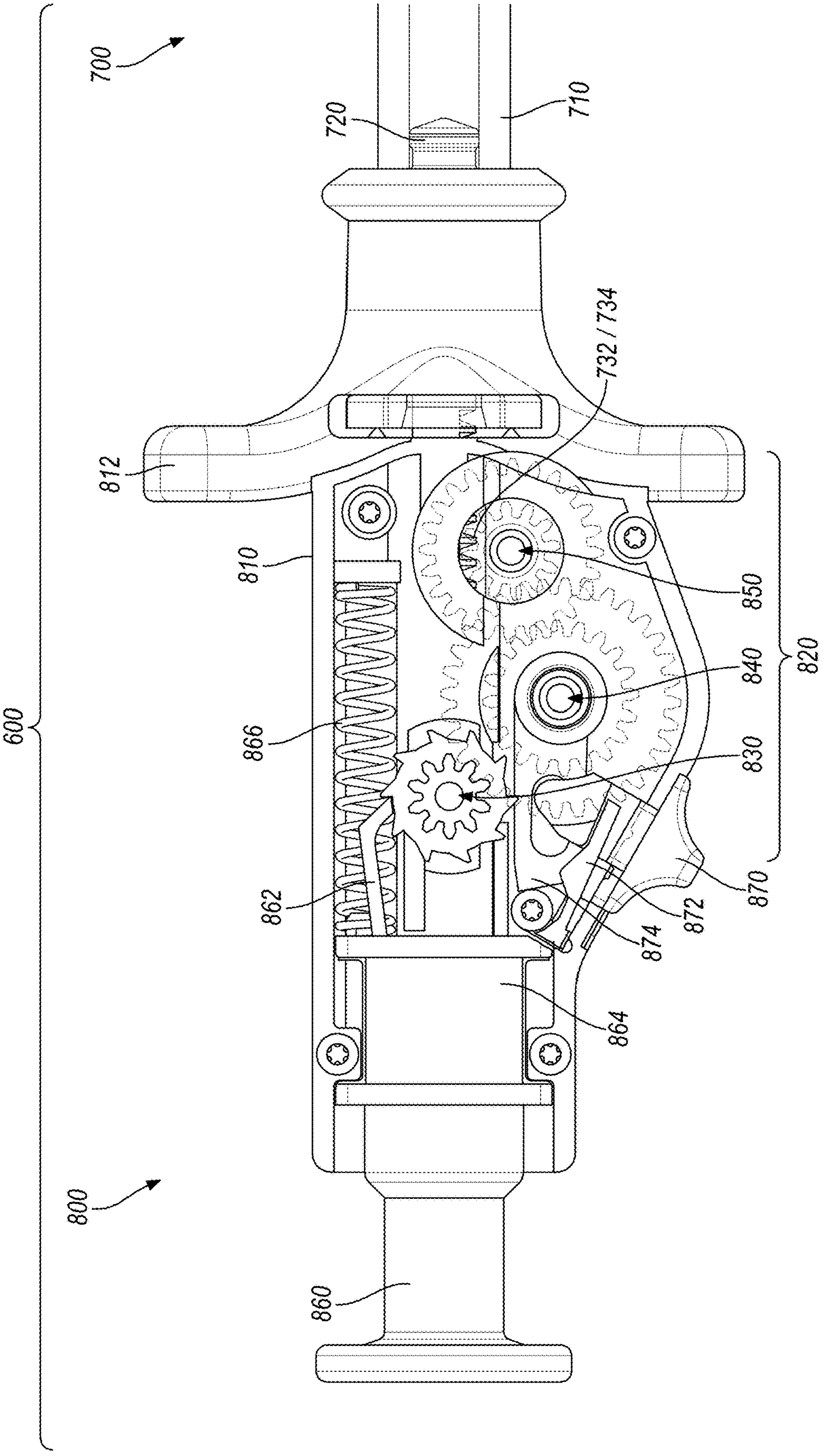
FIG. 13 is a detailed slide view of a multiple site/serial injection system in an end of dose configuration with a portion of the system body omitted to show internal components according to some embodiments.

FIG. 13 is a detailed slide view of a multiple site/serial injection system 600 in an end of dose configuration (see FIG. 10) with a portion of the reusable portion body 810 omitted to show internal components according to some embodiments. The multiple site/serial injection system can be moved from the ready for dose configuration to the end of dose configuration by a distally directed force being applied to the thumbpad member 860 to move the thumbpad member 860 distally relative to the reusable portion body 810 to a distal/end of dose position. Moving the thumbpad member 860 distally moves the plunger member 730 and the stopper member 720 distally relative to the disposable portion body 710 a predetermined distance to eject/inject a predetermined dose (e.g., 10 μl) of fluid/medication from an interior of the disposable portion body 710. Upon release of the thumbpad member 860 the multiple site/serial injection system 600 is configured to reset and deliver another sequential dose on the next press of the thumbpad member 860. The multiple site/serial injection system 600 may be configured to give one dose with one press of the thumbpad member 860 or may be configured to give two or more doses with one press of the thumbpad member 860.

Moving the thumbpad member 860 distally compresses the spring 866 to bias the thumbpad member 860 to move proximally. Moving the thumbpad member 860 distally also causes the pawl 862 to engage the large diameter sprocket gear 834 to rotate the sprocket 830. The pawl 862 is configured to engage a first tooth of the large diameter sprocket gear 834 and, with advancement of the thumbpad member 860, rotate the sprocket 830 clockwise a predetermined amount. The pawl 862 may be configured to flex elastically to maintain engagement with the tooth on the large diameter sprocket gear 834. Rotating the sprocket 830 also rotates the reduction gear 840 because the small diameter sprocket gear 832 is geared to the large diameter reduction gear 844 of the reduction gear 840. Rotating the reduction gear 840 also rotates the pinion gear 850 because the small diameter reduction gear 842 of the reduction gear 840 is geared to the large diameter pinion gear 854 of the pinion gear 850. Rotating the pinion gear 850 moves the rack gear 732 and the plunger member 730 axially.

The distal movement of the thumbpad member 860 results from a user applying a directed distally force on the proximal end of the thumbpad member 860. This user applied force is transmitted to the large diameter sprocket gear 834 through the pawl 862. The sprocket 830, reduction gear 840, and the pinion gear 850 are configured to amplify the user applied force which is transmitted to the rack gear 732 of the plunger member 730, moving the plunger member 730 and the intercoupled stopper 720 distally relative to the syringe body 710 to inject the fluid into the patient. The ratio of the injection force to the user applied force is the force advantage. In some embodiments, the force advantage is approximately 5:1 such that, e.g., 2 lbf. of distally directed user applied force on the thumbpad member 860 results in 10 lbf. of distally directed injection force transmitted to the stopper member 720 to inject the fluid into the patient through the needle 742. The sprocket 830, reduction gear 840, and pinion gear 850 may be tuned by increasing their large diameter regions and/or decreasing their small diameter regions to provide a force advantage in a range between approximately 1.5:1 to approximately 20:1.

Rotating the reduction gear 840 also flexes the anti-return ratchet 872, which engages the next tooth of the large diameter reduction gear 844 to prevent rotation of the reduction gear 840 in the opposite direction. This prevents movements of the rack gear 732 in the plunger member 730 proximally in spite of the potential buildup of back pressure in the disposable portion body 710 during fluid/medication delivery. The anti-return ratchet 872 acting to prevent rotation of the reduction gear 840 also prevents rotation in the opposite (e.g., counterclockwise) direction of the large diameter sprocket gear 834.

The anti-return ratchet 872 is configured to provide audible and/or tactile feedback to the user that a dose of fluid/medication has been delivered. The advancement of a first tooth of the large diameter reduction gear 844 of the reduction gear 840 elastically flexes the anti-return ratchet 872 outward from an initial position to a flexed position. Further advancement/rotation of the reduction gear 840 then moves the first tooth of the large diameter reduction gear 844 past the distal end of the anti-return ratchet 872, causing anti-return ratchet 872 to release back (e.g. snap back) to the initial position into engagement with the back side of the first tooth of the large diameter reduction gear 844 and/or the front side of the next sequential tooth of the large diameter reduction gear 844. This releasing of the anti-return ratchet 872 causes an audible and/or tactile click to be heard by the user that corresponds to the delivery of a dose of fluid/medication.

Upon release of the thumbpad member 860 the spring 866 expands from a compressed state to a relaxed state, moving the thumbpad member 860 and intercoupled pawl 862 proximally back to the position at the start of the dosing movement (ready for dose configuration in FIG. 9). The pawl 862 is configured to dis-engage from the previously engaged first tooth of the large diameter sprocket gear 834 and move to a position where, upon the next advancement of the thumbpad member 860, the pawl 862 will engage the next sequential tooth on the large diameter sprocket gear 834 causing an intermittent rotation of the sprocket 830. This intermittent rotation of the sprocket 830 rotates the reduction gear 840, and the intercoupled pinion gear 850 causing intermittent linear movement of the plunger rack gear 732 to move the plunger member 730 and the stopper member 720 distally in discrete intermittent linear motions a predetermined distance relative to the disposable portion body 710 to eject/inject a predetermined dose (e.g., 10 μl) of fluid/medication from an interior of the disposable portion body 710. Multiple predetermined doses (e.g. 100 doses) may be dispensed in this fashion.

Figure 14:
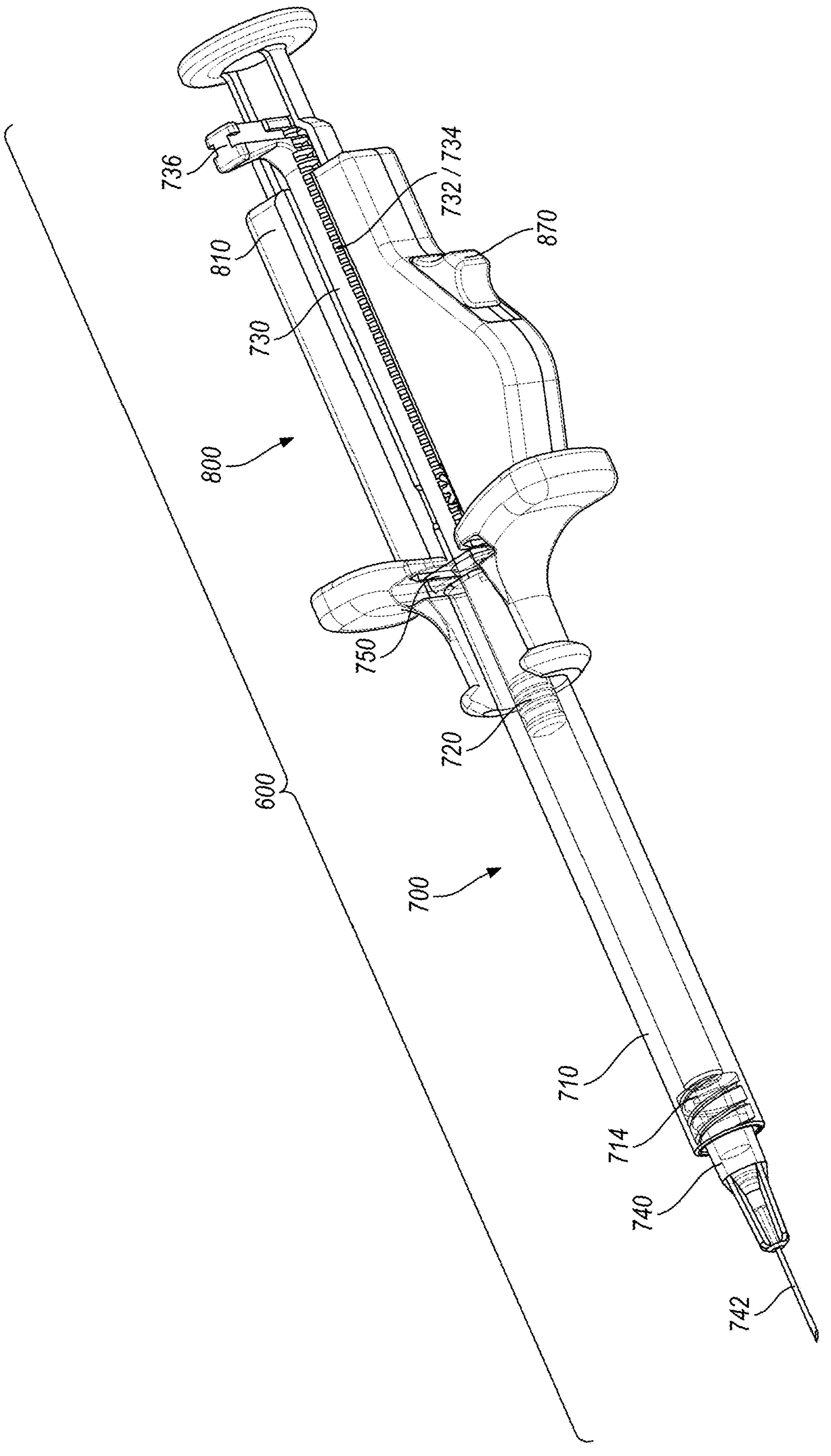
FIG. 14 is a front perspective view of a multiple site/serial injection system in an aspiration mode according to some embodiments.

FIG. 14 is a front perspective view of a multiple site/serial injection system 600 in an aspiration mode according to some embodiments. In the aspiration mode, the mode switch 870 of the reusable portion 800 is in a proximal/aspiration position and the plunger member 730 and stopper member

720 may be moved proximally in the disposable portion body 710 by moving the plunger member handle 736 proximally relative to the reusable portion 800 to draw fluid into the disposable portion body 710.

Figure 15:
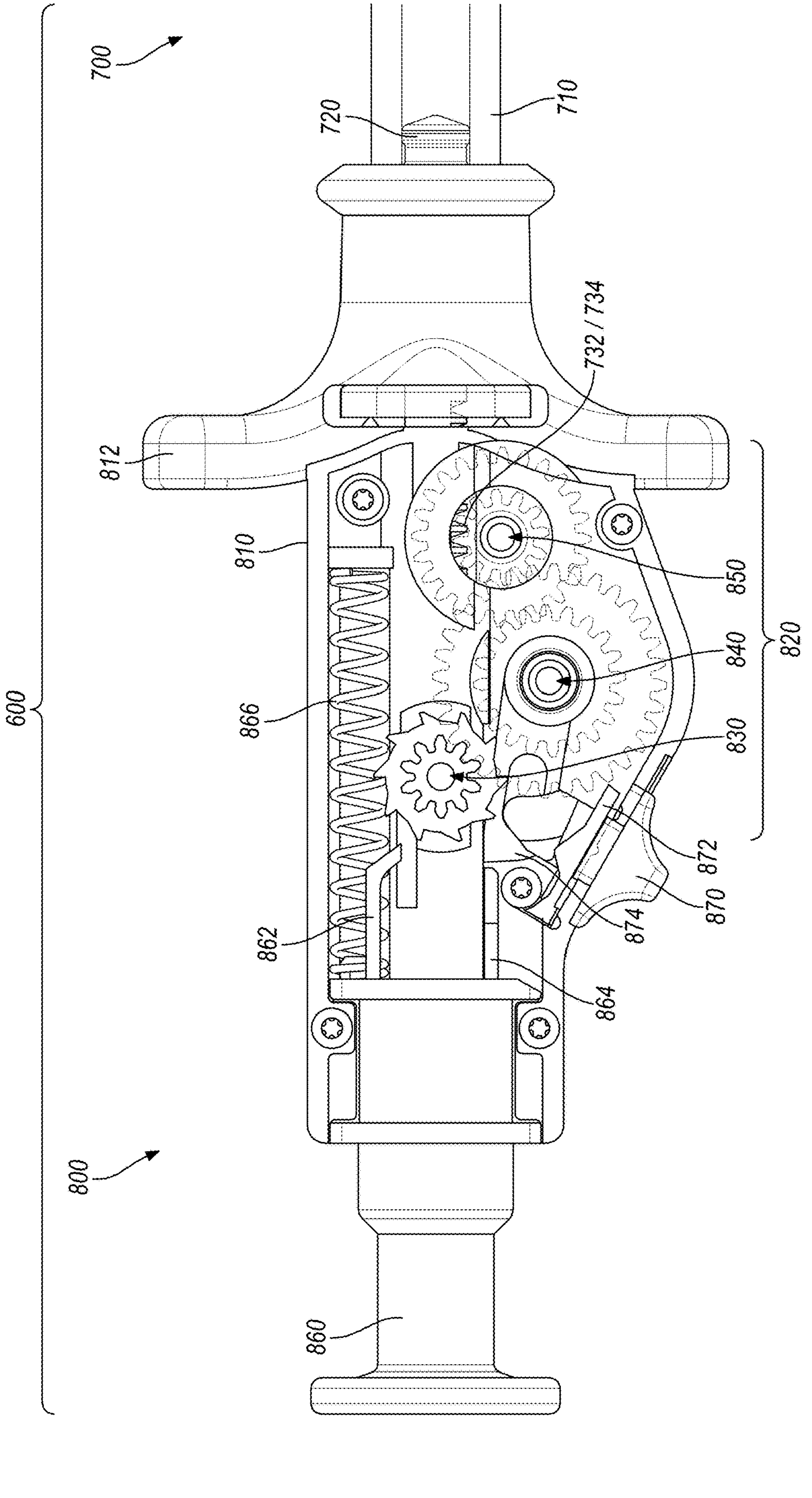
FIG. 15 is a detailed slide view of a multiple site/serial injection system in an aspiration mode with a portion of the system body omitted to show internal components according to some embodiments.

FIG. 15 is a detailed slide view of a multiple site/serial injection system 600 in an aspiration mode (see FIG. 14) with a portion of the reusable portion body 810 omitted to show internal components according to some embodiments. From the distal/dosing position, moving the mode switch 870 into the proximal/aspiration position flexes the anti-return ratchet 872 out of engagement with the reduction gear 840. Removing the anti-return ratchet 872 from the reduction gear 840 allows the gear assembly 820 to freely rotate, thereby allowing free axial movement of the plunger member 730 and the stopper member 720.

Moving the mode switch 870 into the proximal/aspiration position also rotates the thumbpad lockout latch 874 into engagement with the thumbpad lockout tab 864 to prevent the thumbpad member 860 from moving distally, thereby preventing the pawl 862 from engaging the sprocket 830. Preventing the pawl 862 from engaging the sprocket 830 also allows the gear assembly 820 to freely rotate, thereby allowing free axial movement of the plunger member 730 and the stopper member 720. Preventing distal movements of the thumbpad member 860 allows the thumbpad member 860 to provide a counter-force against which to move the plunger member handle 736 proximally during aspiration.

In some embodiments, injection/dispensing systems may be convertible between a traditional/unassisted/manual configuration and a multiple site/serial/assisted configuration. The injection/dispensing system may be shipped in the traditional/unassisted/manual configuration (see FIG. 17). A user may remove certain components (see FIG. 16) to configure the disposable portion 700 for use in a multiple site/serial/assisted injection system such as the multiple site/serial injection system 600 depicted in FIGS. 6 to 15.

Figure 16:
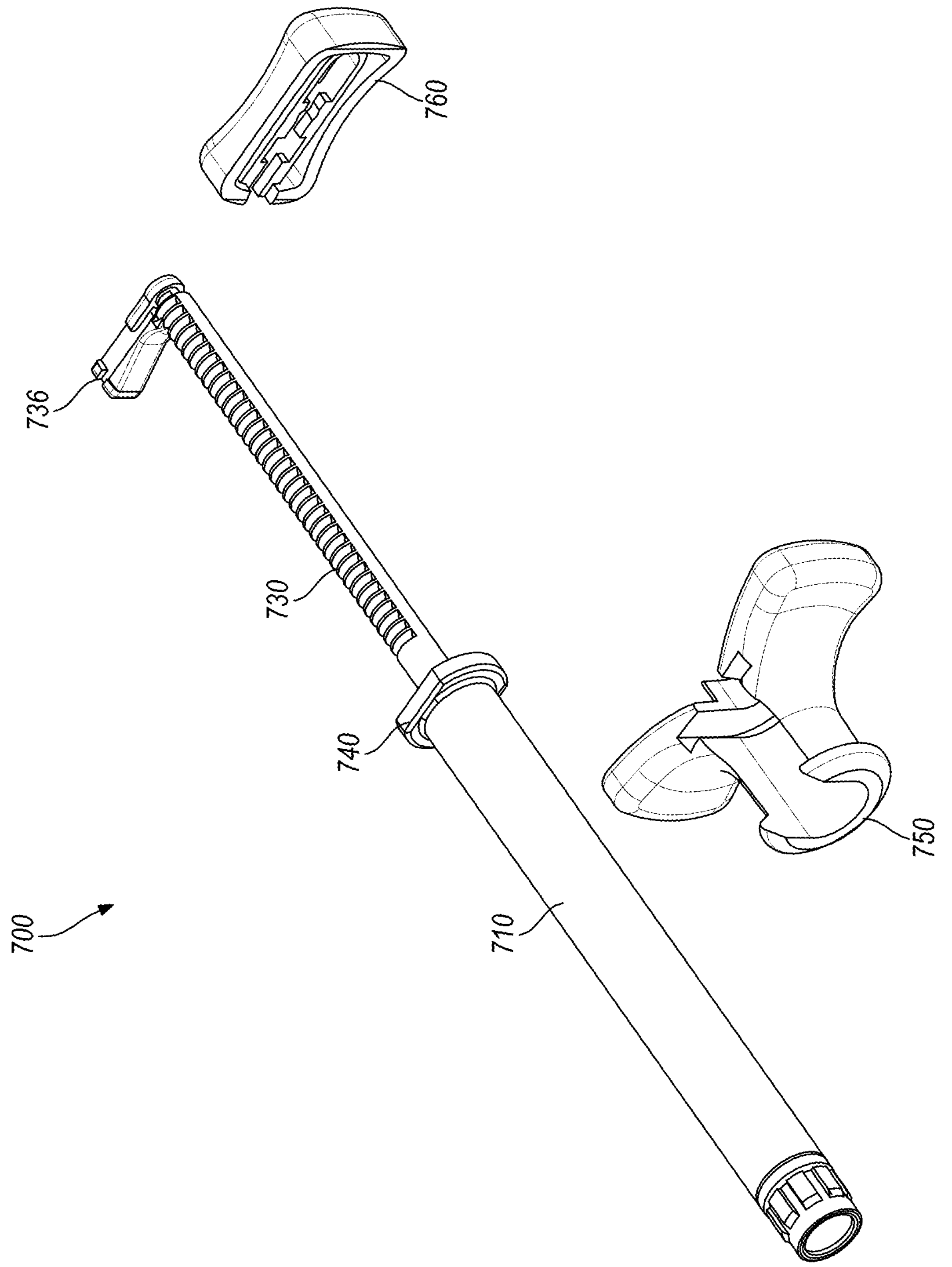
FIG. 16 is a front perspective view of a disposable portion usable with a multiple site/serial injection system and including components to configure the disposable portion for manual use by a user before assembly according to some embodiments.

FIG. 16 is a front perspective view of a disposable portion 700 usable with a multiple site/serial injection system 600 (see FIGS. 6 to 8) and including components to configure the disposable portion 700 for manual use by a user before assembly according to some embodiments. A manual finger flange 750 is configured to be coupled to the disposable portion flange 740 of the disposable portion body 710. A manual thumbpad 760 is configured to be coupled to the plunger member handle 736 of the plunger member 730. The manual thumbpad 760 has a U-shaped channel for sliding onto the plunger member handle 736 of the plunger member 730.

Figure 17:
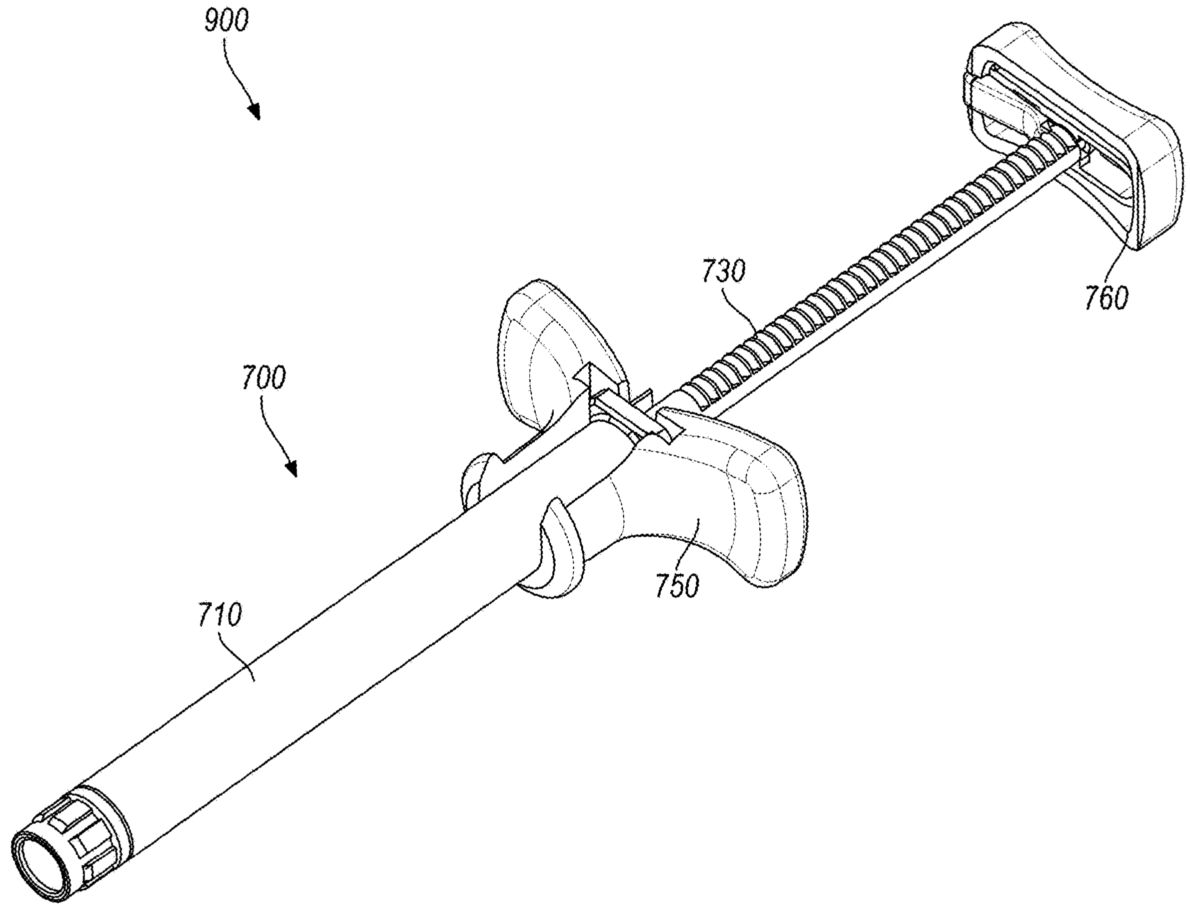
FIG. 17 is a front perspective view of a manual injection/dispensing system including a disposable portion usable with a multiple site/serial injection system and configured for manual use by a user according to some embodiments.

FIG. 17 is a front perspective view of a manual injection/dispensing system 900 including a disposable portion 700 usable with a multiple site/serial injection system 600 and configured for manual use by a user according to some embodiments. The manual injection/dispensing system 900 includes a manual finger flange 750 coupled to the disposable portion body 710 and a manual thumbpad 760 coupled to the plunger member 730.

Figure 18:
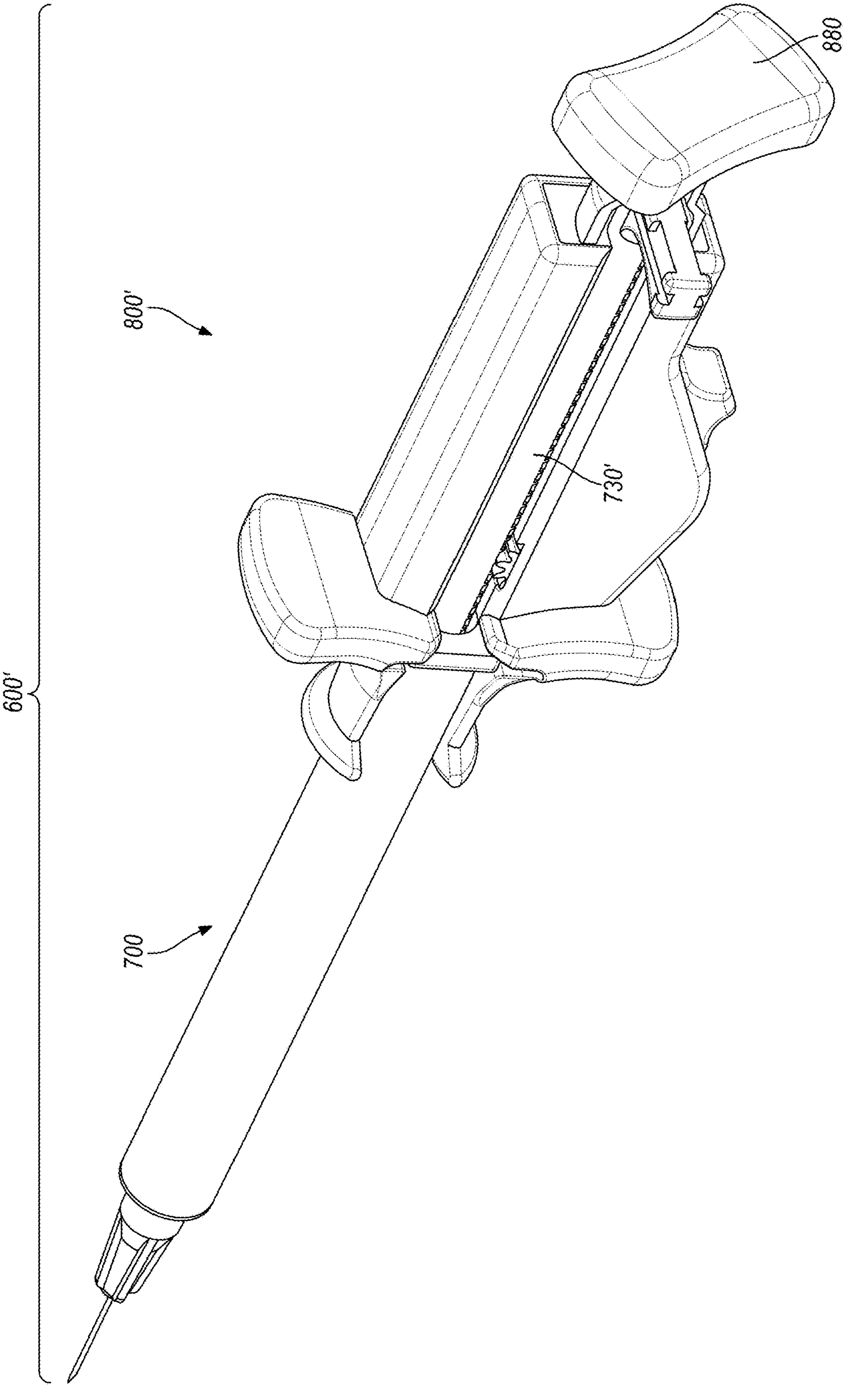
FIG. 18 is a rear perspective view of a multiple site/serial injection system with a rotatable thumbpad according to some embodiments.

FIG. 18 is a rear perspective view of a multiple site/serial injection system 600' with a rotatable thumbpad 880 according to some embodiments. The disposable portion 700 of the multiple site/serial injection system 600' is identical to the disposable portion 700 in the multiple site/serial injection system 600 depicted in FIGS. 6 to 15. The only difference between the reusable portion 800' of the multiple site/serial injection system 600' and the reusable portion 800 in the multiple site/serial injection system 600 depicted in FIGS. 6 to 15 is the replacement of the proximal end of the thumbpad member 860 in FIGS. 6 to 15 with the rotatable thumbpad 880 in FIG. 18. The rotatable thumbpad 880 is rotatable relative to the plunger member 730' to improve user comfort and ergonomics.

Figure 19A:
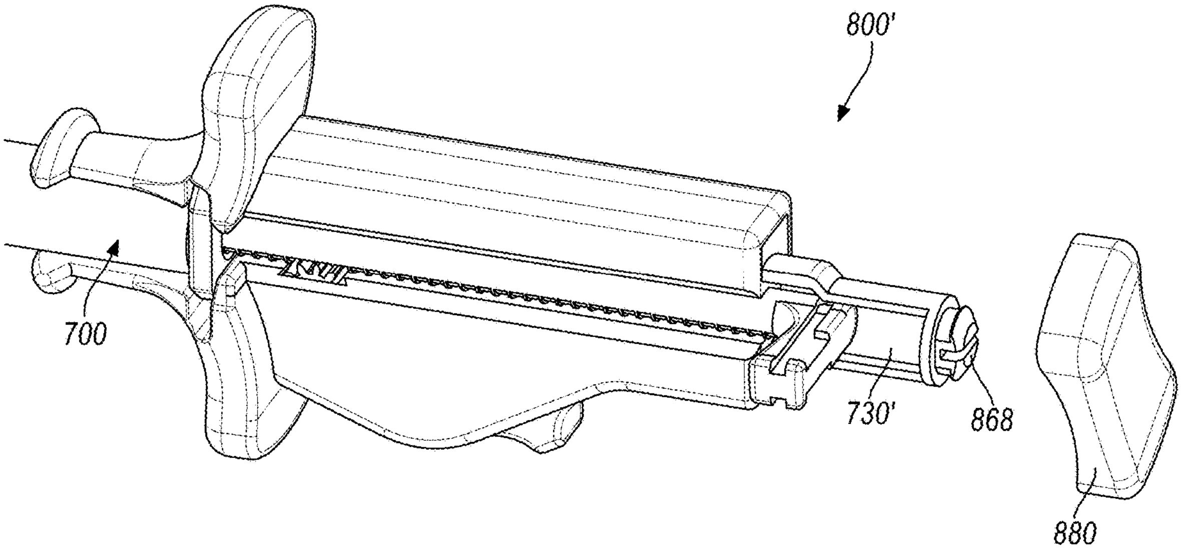
FIG. 19A is a partially exploded perspective view of a multiple site/serial injection system with a rotatable thumbpad according to some embodiments.

FIG. 19A is a partially exploded perspective view of a multiple site/serial injection system 600' with a rotatable thumbpad 880 according to some embodiments. Instead of ending in a traditional thumbpad, the plunger member 730' in FIG. 19A ends in a barbed peg 868 at a proximal end thereof. The rotatable thumbpad 880 is rotatably coupled to the barbed peg 868.

Figure 19B:
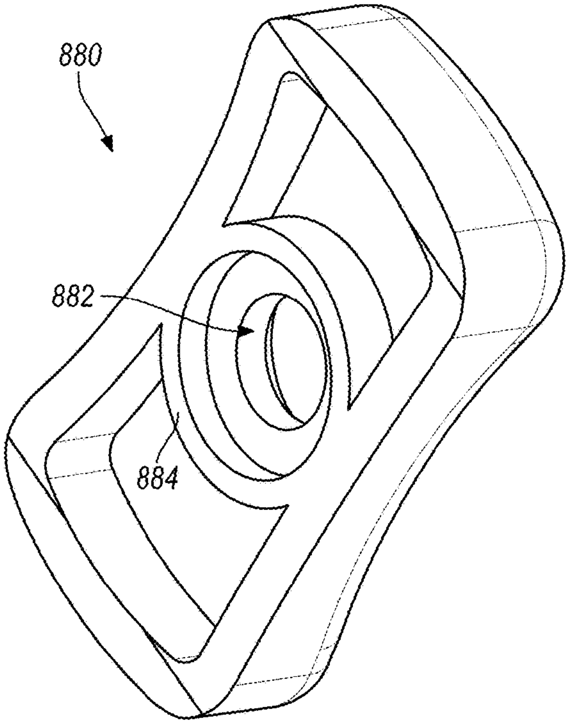
FIG. 19B is a front perspective view of a rotatable thumbpad for use with a multiple site/serial injection system with a rotatable thumbpad according to some embodiments.

FIG. 19B is a front perspective view of a rotatable thumbpad 880 for use with a multiple site/serial injection system 600' according to some embodiments. The rotatable thumbpad 880 has an oblong shape. The rotatable thumbpad 880 defines an undercut hole 882 at a distal end thereof configured to receive the barbed peg 868 of the plunger member 730'. The rotatable thumbpad 880 may define a plurality of bumps to provide pre-set rotational positions. The rotatable thumbpad 880 also defines a cylindrical guide surface 884 at a distal end thereof to provide a tight fit between the rotatable thumbpad 880 and the plunger member 730'. The tight fit may provide some resistance to rotation after a user sets a comfortable rotational position.

Figure 20:
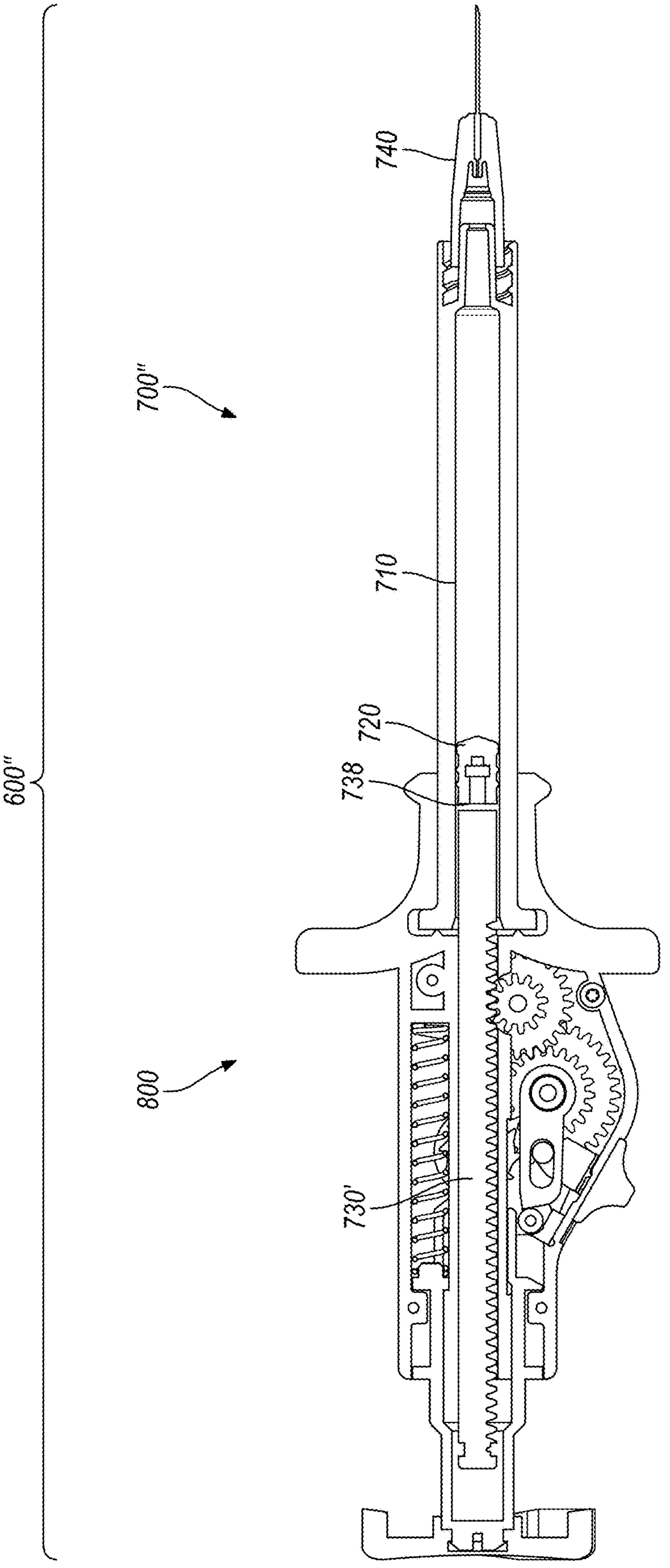
FIG. 20 is a longitudinal cross-sectional view of a multiple site/serial injection system with a plunger member having a flat distal end according to some embodiments.

FIG. 20 is a longitudinal cross-sectional view of a multiple site/serial injection system 600" with a plunger member 730" having a flat distal end 738 according to some embodiments. The reusable portion 800 of the multiple site/serial injection system 600" is identical to the reusable portion 800 in the multiple site/serial injection system 600 depicted in FIGS. 6 to 15. The only difference between the disposable portion 700" of the multiple site/serial injection system 600" and the disposable portion 700 in the multiple site/serial injection system 600 depicted in FIGS. 6 to 15 is the elimination of the spike/threaded connector at the distal end of the plunger member 730 in FIGS. 6 to 15. Eliminating the spike/threaded connector at the distal end of the plunger member 730 results in a flat distal end 738 without any protrusions for connecting to the stopper member 720.

While the dispensing and/or injection systems depicted and described herein include syringes with Luer connectors, the multiple site dispensing and/or injection systems described herein can be used with staked needles, cartridges, and auto injectors, etc. The multiple site dispensing and/or injection systems described herein can also be used with safe dispensing and/or injection systems such as those described in U.S. patent application Ser. No. 14/696,342, the contents of which have been previously incorporated by reference herein.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, ETFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for injection, comprising:
- a disposable portion, comprising
  - a syringe body having proximal and distal ends, a syringe interior, and a disposable portion flange at the proximal end thereof,
  - an injectable fluid disposed in the syringe interior,
  - a stopper member disposed in the syringe interior, and
  - a plunger member coupled to the stopper member, wherein the plunger member defines a rack gear comprising a plurality of rack gear teeth; and
- a reusable portion configured to be removably coupled to the disposable portion, the reusable portion comprising
  - a gear assembly comprising a pinion gear configured to sequentially advance the plunger member distally by a predetermined distance, and
  - a finger flange coupled to the disposable portion flange,
- wherein the gear assembly comprises
  - a sprocket, and
  - a reduction gear operatively coupling the sprocket to the pinion gear,
- wherein the reusable member comprises a thumbpad member,
- wherein the thumbpad member defines a pawl at a distal end thereof, and
- wherein the pawl is operatively coupled to the sprocket of the gear assembly.

2. The system of claim 1, wherein the disposable portion is a syringe.

3. The system of claim 1, wherein the plunger member comprises a plunger member handle coupled to a proximal end of the plunger member.

4. The system of claim 3, wherein the plunger member has a protrusion configured to be disposed in the stopper member to couple the stopper member to the plunger member.

5. The system of claim 3, wherein the plunger member has a flat distal end without any protrusions configured to be disposed in the stopper member.

6. The system of claim 1, wherein the reduction gear comprises a large diameter reduction gear and a small diameter reduction gear,
- wherein the sprocket is configured to act on the large diameter reduction gear, and
- wherein the small diameter reduction gear is configured to act on the pinion gear.

7. The system of claim 1, wherein the pinion gear comprises a large diameter pinion gear and a small diameter pinion gear,
- wherein the reduction gear is configured to act on the large diameter pinion gear, and
- wherein the small diameter pinion gear is configured to act on the rack gear on the plunger member.

8. The system of claim 1, wherein the reusable member comprises a thumbpad lockout tab and a thumbpad lockout latch.

9. The system of claim 8, wherein the sprocket comprises a large diameter sprocket gear and a small diameter sprocket gear, wherein the pawl is configured to act on the large diameter sprocket gear, and wherein the small diameter sprocket gear is configured to act on the reduction gear.

10. The system of claim 8, wherein the reusable member comprises a return spring configured to move the thumbpad member proximally after the thumbpad member is advanced distally.

11. The system of claim 10, wherein the reusable member comprises an anti-return ratchet configured to prevent backwards rotation of the reduction gear to thereby prevent proximal movement of the plunger member.

12. The system of claim 11, wherein the reusable member comprises a mode switch configured to change the system between a dosing mode and an aspiration mode, wherein actuating the mode switch to the aspiration mode moves the anti-return ratchet out of engagement with the reduction gear to allow free rotation of the reduction gear and the pinion gear and proximal movement of the plunger member, and moves the thumbpad lockout latch into engagement with the thumbpad lockout tab to prevent distal movement of the thumbpad member.

13. The system of claim 12, wherein actuating the mode switch to the dosing mode moves the anti-return ratchet into engagement with the reduction gear to prevent free rotation of the reduction gear and the pinion gear and free proximal movement of the plunger member, and moves the thumbpad lockout latch out of engagement with the thumbpad lockout tab to allow distal movement of the thumbpad member.

14. The system of claim 1, wherein the disposable portion and the reusable portion are configured to allow a user to insert the disposable portion into the reusable portion.

15. The system of claim 14, further comprising:

a manual finger flange configured to be coupled to the disposable portion flange; and a manual thumbpad configured to be coupled to a proximal end of the plunger member, wherein coupling the manual finger flange and the manual thumbpad to the disposable portion flange and the proximal end of the plunger member configures the disposable portion for manual use by a user.

16. The system of claim 1, wherein the plunger member comprises a barbed peg at a proximal end thereof, the system further comprising an oblong shaped free-spinning thumbpad rotatably coupled to the barbed peg at the proximal end of the plunger member.

* * * * *